United States Patent
McDevitt et al.

(10) Patent No.: US 7,012,169 B2
(45) Date of Patent: Mar. 14, 2006

(54) DISPOSABLE FINGER SLEEVE FOR APPENDAGES

(75) Inventors: Jason P. McDevitt, Alpharetta, GA (US); Michael S. Brunner, Roswell, GA (US); Kaiyuan Yang, Roswell, GA (US); Jark Lau, Roswell, GA (US); John Metz, Vernon, CT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/826,371

(22) Filed: Apr. 4, 2001

(65) Prior Publication Data

US 2003/0050589 A1    Mar. 13, 2003

Related U.S. Application Data

(60) Provisional application No. 60/195,517, filed on Apr. 6, 2000, provisional application No. 60/195,071, filed on Apr. 6, 2000, provisional application No. 60/194,929, filed on Apr. 6, 2000, provisional application No. 60/195,072, filed on Apr. 6, 2000, provisional application No. 60/194,930, filed on Apr. 6, 2000, provisional application No. 60/257,137, filed on Dec. 20, 2000.

(51) Int. Cl.
*A61F 13/00* (2006.01)

(52) U.S. Cl. .................... 602/41; 42/43; 42/44; 42/45; 42/60; 42/61

(58) Field of Classification Search ............ 602/41–47, 602/22, 63, 48, 60–61
See application file for complete search history.

(56) References Cited

U.S. PATENT DOCUMENTS 1,896,941 A    2/1933    Cohen (Continued)

FOREIGN PATENT DOCUMENTS

EP    0303528    7/1988

(Continued)

OTHER PUBLICATIONS

*Polymer Blends & Composites;* John A. Manson & Leslie H. Sperling ©1976; Plenum Press; IBSN 0-306-30831-2; pp 273-277.

(Continued)

*Primary Examiner*—Vincent Millin
*Assistant Examiner*—Lalita M. Hamilton
(74) *Attorney, Agent, or Firm*—Dority & Manning, P.A.

(57) ABSTRACT

A device that can be used to treat appendage ailments is provided. The device, or appendage sleeve, can be used for wounds, cuts, and blisters, as well as joint related ailments, such as arthritis and carpal tunnel syndrome. In some instances, the appendage sleeve can at least partially made from an elastomeric material, such as an elastomeric nonwoven, so that the sleeve can more aptly fit onto a finger or toe. Furthermore, the sleeve can also possess a barrier that is liquid impermeable, but vapor permeable so that the finger or toe of a user is more comfortable. Various additives can be applied to the sleeve to aid for therapeutic purposes.

35 Claims, 4 Drawing Sheets

U.S. PATENT DOCUMENTS

| | | |
|---|---|---|
| 2,041,262 A | 5/1936 | Ness |
| 2,179,614 A | 11/1939 | Cohen |
| 2,599,191 A | 6/1952 | Meunier |
| 2,646,796 A * | 7/1953 | Scholl .................. 128/157 |
| 2,673,365 A | 3/1954 | Moor, Jr. |
| 2,882,528 A | 4/1959 | Tassie |
| 2,925,605 A | 2/1960 | Wheeler |
| 3,070,102 A | 12/1962 | MacDonald |
| 3,124,824 A | 3/1964 | Lutz |
| 3,263,681 A | 8/1966 | Nechtow et al. |
| 3,298,507 A | 1/1967 | Micciche |
| 3,338,992 A | 8/1967 | Kinney |
| 3,341,394 A | 9/1967 | Kinney |
| 3,348,541 A * | 10/1967 | Loebeck .................. 128/157 |
| 3,368,668 A | 2/1968 | Micciche |
| 3,448,478 A | 6/1969 | Nash et al. |
| 3,485,706 A | 12/1969 | Evans |
| 3,502,763 A | 3/1970 | Hartman |
| 3,542,615 A | 11/1970 | Dobo et al. |
| 3,589,823 A | 6/1971 | Hendrickson |
| 3,675,264 A | 7/1972 | Storandt |
| 3,692,618 A | 9/1972 | Dorschner |
| 3,696,821 A | 10/1972 | Adams, IV |
| 3,802,817 A | 4/1974 | Matsuki et al. |
| 3,849,241 A | 11/1974 | Butin et al. |
| 3,853,412 A | 12/1974 | Griffin |
| 3,855,046 A | 12/1974 | Hansen et al. |
| 3,902,509 A | 9/1975 | Tundermann et al. |
| 3,905,113 A | 9/1975 | Jacob |
| 3,952,867 A | 4/1976 | McCord |
| 3,982,298 A | 9/1976 | Ota |
| 4,041,203 A | 8/1977 | Brock et al. |
| 4,084,586 A | 4/1978 | Hettick |
| 4,121,312 A * | 10/1978 | Penney .................. 441/57 |
| 4,269,181 A | 5/1981 | Delannoy |
| 4,323,534 A | 4/1982 | DesMarais |
| 4,335,731 A | 6/1982 | Bora, Jr. |
| 4,340,563 A | 7/1982 | Appel |
| 4,414,970 A | 11/1983 | Berry |
| 4,616,374 A | 10/1986 | Novogrodsky |
| 4,617,694 A | 10/1986 | Bori |
| 4,643,725 A | 2/1987 | Schlesser et al. |
| 4,643,791 A | 2/1987 | Jurrius et al. |
| 4,655,760 A | 4/1987 | Morman et al. |
| 4,657,802 A | 4/1987 | Morman et al. |
| 4,660,228 A | 4/1987 | Ogawa et al. |
| 4,663,220 A | 5/1987 | Wisneski et al. |
| 4,665,901 A | 5/1987 | Spector |
| 4,707,398 A | 11/1987 | Boggs |
| 4,720,415 A | 1/1988 | Vander Wielen et al. |
| 4,724,184 A | 2/1988 | Killian et al. |
| 4,733,410 A | 3/1988 | Glotkin |
| 4,741,949 A | 5/1988 | Morman et al. |
| 4,766,029 A | 8/1988 | Brock et al. |
| 4,781,966 A | 11/1988 | Taylor |
| 4,789,699 A | 12/1988 | Kieffer et al. |
| 4,795,668 A | 1/1989 | Krueger et al. |
| 4,803,117 A | 2/1989 | Daponte |
| 4,820,572 A | 4/1989 | Killian et al. |
| 4,825,470 A | 5/1989 | Horio |
| 4,828,556 A | 5/1989 | Braun et al. |
| 4,834,738 A | 5/1989 | Kielpikowski et al. |
| 4,858,245 A * | 8/1989 | Sullivan et al. .................. 2/21 |
| 4,875,247 A | 10/1989 | Berg |
| 4,884,581 A | 12/1989 | Rescigno |
| 4,920,974 A * | 5/1990 | Roth et al. .................. 128/759 |
| 4,923,742 A | 5/1990 | Killian et al. |
| 4,926,851 A * | 5/1990 | Bulley .................. 602/60 |
| 4,965,122 A | 10/1990 | Morman |
| D313,317 S | 1/1991 | Brunner et al. |
| 4,981,747 A | 1/1991 | Morman |
| 4,998,978 A | 3/1991 | Varum |
| 5,036,551 A | 8/1991 | Dailey et al. |
| 5,057,368 A | 10/1991 | Largman et al. |
| 5,068,941 A | 12/1991 | Dunn |
| 5,093,422 A | 3/1992 | Himes |
| 5,108,820 A | 4/1992 | Kaneko et al. |
| 5,108,827 A | 4/1992 | Gessner |
| 5,114,781 A | 5/1992 | Morman |
| 5,116,662 A | 5/1992 | Morman |
| 5,120,758 A * | 6/1992 | Satoh .................. 9/60 |
| 5,123,113 A | 6/1992 | Smith |
| 5,133,971 A | 7/1992 | Copelan et al. |
| 5,169,706 A | 12/1992 | Collier, IV et al. |
| 5,181,914 A * | 1/1993 | Zook .................. 604/307 |
| 5,213,428 A | 5/1993 | Salman |
| 5,226,992 A | 7/1993 | Morman |
| 5,228,433 A | 7/1993 | Rosen |
| 5,277,976 A | 1/1994 | Hogle et al. |
| 5,280,661 A | 1/1994 | Brown |
| 5,287,584 A | 2/1994 | Skinner |
| 5,294,482 A | 3/1994 | Gessner |
| 5,304,599 A | 4/1994 | Himes |
| 5,320,531 A | 6/1994 | Delizo-Madamba |
| 5,332,613 A | 7/1994 | Taylor et al. |
| 5,336,545 A | 8/1994 | Morman |
| 5,336,552 A | 8/1994 | Strack et al. |
| 5,348,153 A | 9/1994 | Cole |
| 5,356,005 A | 10/1994 | Burrello |
| 5,362,306 A * | 11/1994 | McCarver et al. .................. 602/60 |
| 5,382,400 A | 1/1995 | Pike et al. |
| 5,383,846 A | 1/1995 | Short |
| 5,389,202 A | 2/1995 | Everhart et al. |
| 5,439,487 A | 8/1995 | Stanitzok |
| 5,440,774 A | 8/1995 | Cole |
| 5,445,825 A | 8/1995 | Copelan et al. |
| 5,464,688 A | 11/1995 | Timmons et al. |
| 5,466,410 A | 11/1995 | Hills |
| 5,474,525 A | 12/1995 | Blott |
| 5,486,381 A | 1/1996 | Cleveland et al. |
| 5,487,201 A | 1/1996 | Hansen et al. |
| 5,502,863 A | 4/1996 | Perkins |
| 5,503,908 A | 4/1996 | Faass |
| 5,507,641 A | 4/1996 | Cline |
| 5,524,764 A | 6/1996 | Kaufman et al. |
| 5,529,665 A | 6/1996 | Kaun |
| 5,541,388 A | 7/1996 | Gadd |
| 5,554,076 A | 9/1996 | Clark |
| 5,591,510 A | 1/1997 | Junker et al. |
| 5,636,405 A | 6/1997 | Stone et al. |
| 5,678,273 A | 10/1997 | Porcelli |
| 5,752,926 A * | 5/1998 | Larson et al. .................. 602/7 |
| 5,765,252 A | 6/1998 | Carr |
| 5,766,248 A | 6/1998 | Donovan |
| 5,770,229 A * | 6/1998 | Tanihara et al. .................. 424/488 |
| 5,771,522 A | 6/1998 | Carmody |
| 5,794,774 A | 8/1998 | Porcelli |
| 5,804,021 A * | 9/1998 | Abuto et al. .................. 156/252 |
| 5,819,765 A | 10/1998 | Mittiga |
| 5,826,599 A | 10/1998 | Adams |
| 5,834,002 A | 11/1998 | Athanikar |
| 5,875,513 A | 3/1999 | Reinold |
| 5,909,739 A | 6/1999 | Masrour-Rad |
| 5,911,319 A | 6/1999 | Porcelli et al. |
| 5,953,783 A | 9/1999 | Hahn |
| 6,019,773 A | 2/2000 | Denmark |
| 6,105,587 A | 8/2000 | Dunn |
| 6,112,356 A | 9/2000 | Hashey |
| 6,139,514 A * | 10/2000 | Benson .................. 602/63 |
| 6,336,461 B1 | 1/2002 | Martinez |
| 6,409,059 B1 | 6/2002 | Calvert |
| 6,420,624 B1 | 7/2002 | Kawase |
| 6,494,767 B1 | 12/2002 | Fisher |

| | | | |
|---|---|---|---|
| 6,508,602 B1 | 1/2003 | Gruenbacher et al. | |
| 2002/0170133 A1 | 11/2002 | McDevitt et al. | |

FOREIGN PATENT DOCUMENTS

| | | |
|---|---|---|
| EP | 0638277 A1 | 2/1995 |
| EP | 0985364 A2 | 3/2000 |
| EP | 0985364 A3 | 3/2000 |
| EP | 0985364 B1 | 3/2000 |
| GB | 2099305 A | 12/1982 |
| GB | 2227938 A | 8/1990 |
| WO | WO87/07122 | 12/1987 |
| WO | WO92/03947 | 3/1992 |
| WO | WO95/31154 | 11/1995 |
| WO | WO99/55271 | 11/1999 |

OTHER PUBLICATIONS

Medical Textiles, Nov. 1999 "Crimped Bristle Toothbrush".

"Nonwoven Removes Stains", "Dental Floss".

Tetra Medical Supply Corp.; Product Information; Jan. 4, 2000; www.tetramed.com/dress.htm.

Spandage; Product Information; Jan. 4, 2000; spandage.com/main.htm.

FootSmark Products; Product Information-Toe Caps & DigiCushions; Jan. 4, 2000; www.footsmart.com.

U.S. Appl. No. 09/826,413, filed Apr. 4, 2001, McDevitt, et al., Finger Glove.

Abstract of Japanese Patent No. 10243818, Sep. 14, 1998.

* cited by examiner

DISPOSABLE FINGER SLEEVE FOR APPENDAGES

RELATED APPLICATIONS

This application is based upon the following provisional applications:

U.S. Ser. No. 60/195,517, filed on Apr. 6, 2000; U.S. Ser. No. 60/195,071, filed on Apr. 6, 2000; U.S. Ser. No. 60/194,929, filed on Apr. 6, 2000; U.S. Ser. No. 60/195,072, filed on Apr. 6, 2000; U.S. Ser. No. 60/194,930, filed on Apr. 6, 2000; and U.S. Ser. No. 60/257,137, filed on Dec. 20, 2000.

BACKGROUND OF THE INVENTION

A variety of appendage ailments and injuries have continuously plagued people over the years. For example, fingers and toes can become wounded, cut, or blistered. Moreover, the joints of fingers and toes can suffer from a number of ailments, such as arthritis or carpal tunnel syndrome, or become jammed, sprained, hyper-extended, dislocated, or broken. In addition, fingers and toes can also be afflicted with warts, or corns. Further, toenails can frequently suffer from fungal infection, referred to as onychomycosis. Additionally, hikers, athletes, joggers, and others often suffer from "blacktoe", the result of repetitive, forceful striking of the end of a shoe or boot with a toenail.

Traditionally, these appendage ailments have been treated in a variety of ways. For instance, when treating finger cuts or wounds, bandages can be wrapped around the wound to allow healing. Typically, these bandages have a tacky surface formed by an adhesive so that the bandages can stick to a finger for a certain period of time. One example of such bandages are BAND-AIDS, made by Johnson & Johnson, which are commonly used to cover finger and toe wounds. In some instances, these bandages can also deliver an active ingredient to the wound or cut to aid in healing. However, these bandages are not generally comfortable to a user, and can often easily slip off the appendage. For this reason, bandages with enhanced flexibility and elasticity have been developed. Moreover, bandages having various other properties have also been described. For instance, U.S. Pat. No. 4,414,970 to Berry describes a moisture vapor transmitting elastic bandage, while U.S. Pat. No. 5,503,908 to Faass describes a self-adhesive, elastic composite material.

In addition to treating cuts and wounds, various techniques have been developed to treat joint ailments, such as jammed fingers, arthritis, and "trigger finger". For example, to treat a jammed finger, cloth-like wraps and finger sleeves have been developed to be placed around an ailing joint to provide warmth and support thereto. Similar products have also been utilized to treat arthritis. For instance, a finger sleeve marketed as "FINGERS" has been developed to treat arthritis in appendages. This product is primarily designed to provide support to ailing joints, but does not generally deliver active additives, such as medications, to the joint. Moreover, these products are also non-disposable. In addition, these devices are often difficult to process using high speed manufacturing techniques.

Other additional tubular products have also been developed as support mechanisms and wound dressings. For instance, "TUBE GAUZE", which is commercially available from Tetra Medical Supply Company, is a seamless cotton tubular gauze sold in various sizes. Moreover, "SPANDAGE", which is commercially available from Medi-Tech International, is an elastic tubular bandage made from elastic and polyester fibers. Examples of other available products include "TOE CAPS" and "DIGI-CUSHIONS", which are sold by Footsmart. "DIGI-CUSHIONS" are believed to be woven tubes (lycra-like) applied with a polymer gel on their inner layer. "TOE CAPS" are believed to be a foam product used to relieve toe pain and pressure when worn over the tip of a toe. However, the devices mentioned above are often difficult to process using high speed manufacturing techniques.

Moreover, other tubular products have also been developed. For instance, U.S. Pat. No. 4,084,586 to Hettich describes a tubular support for enclosing a body member, in which the tubular support is elastic and stretchable in all directions. Further, U.S. Pat. No. 4,269,181 to Delannoy describes a one-piece tubular dressing made of a woven hydrophilic material. In addition, U.S. Pat. No. 5,474,525 to Blott describes a tubular undercast padding for a body-immobilizing cast comprising a lofted non-woven fabric formed from a fabric material.

SUMMARY OF THE INVENTION

Definitions

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes referred to as multiconstituent fibers. Fibers of this general type are discussed in, for example, U.S. Pat. Nos. 5,108,827 and 5,294,482 to Gessner. Biconstituent fibers are also discussed in the textbook *Polymer Blends and Composites* by John A. Manson and Leslie H. Sperling, copyright 1976 by Plenum Press., a division of Plenum Publishing Corporation of New York, IBSN 0-306-30831-2, at pages 273 through 277.

As used herein, the term "breathable" means pervious to water vapor and gases. In other words, "breathable barriers" and "breathable films" allow water vapor to pass therethrough. For example, "breathable" can refer to a film or laminate having water vapor transmission rate (WVTR) of at least about 300 g/m$^2$/24 hours measured using ASTM Standard E96-80, upright cup method, with minor variations as described in the following Test Procedure.

A measure of the breathability of a fabric is the water vapor transmission rate (WVTR) which, for sample materials, is calculated essentially in accordance with ASTM Standard E96-80 with minor variations in test procedure as set forth hereinbelow. Circular samples measuring three inches in diameter are cut from each of the test materials, and tested along with a control, which is a piece of "CELGARD" 2500 sheet from Celanese Separation Products of Charlotte, N.C. "CELGARD" 2500 sheet is a microporous polypropylene sheet. Three samples are prepared for each material. The test dish is a No. 60-1 Vapometer pan distributed by Thwing-Albert Instrument Company of Philadelphia, Pa. 100 milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 cm diameter circle having an exposed area of approximately 33.17 square centimeters. The pans are placed in a forced air oven at 100° F. (32° C.) for one hour to equilibrate. The oven is a constant temperature oven with external air circulating through it to prevent water vapor accumulation inside. A suitable forced air oven is, for example, a Blue M Power-O-Matic 600 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows: Test WVTR=(grams weight loss over 24 hours)×(315.5 g/m$^2$/24 hours).

The relative humidity within the oven is not specifically controlled. Under predetermined set conditions of 100° F. (32° C.) and ambient relative humidity, the WVTR for the "CELGARD" 2500 control has been defined to be 5000 grams per square meter for 24 hours. Accordingly, the control sample was run with each test and the preliminary test values were corrected to set conditions using the following equation: WVTR=(test WVTR/control WVTR)×(5000 g/m$^2$/24 hrs.).

As used herein, the term "conjugate fibers" refers to fibers which have been formed from at least two polymers extruded from separated extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement, wherein one polymer is surrounded by another or may be a side by side arrangement, a pie arrangement or an "islands-in-the-sea" arrangement. Conjugate fibers are taught by U.S. Pat. No. 5,108,820 to Kaneko et al., and U.S. Pat. No. 4,795,668 to Krueger et al., U.S. Pat. No. 5,336,552 to Strack et al. Conjugate fibers are also taught in U.S. Pat. No. 5,382,400 to Pike et al. and may be used to produced crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75, or any other desired ratios. The fibers may also have shapes such as those described in U.S. Pat. No. 5,277,976 to Hogle et al. U.S. Pat. No. 5,466,410 to Hill, U.S. Pat. No. 5,069,970 to Largman et al., and U.S. Pat. No. 5,057,368 to Largman et al., which describe fibers with unconventional shapes.

As used herein, the terms "elastic" and "elastomeric" are generally used to refer to materials that, upon application of a force, are stretchable to a stretched, biased length which is at least about 125%, or one and one fourth times, its relaxed, unstretched length, and which will retract at least about 50% of its elongation upon release of the stretching, biasing force.

As used herein, the term "filament" refers to a generally continuous strand that has a large ratio of length to diameter, such as, for example, a ratio of 1000 or more.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited on a collecting surface.

As used herein, a "moisture barrier" refers to any material that is relatively impermeable to the transmission of fluids, i.e. a fabric having a moisture barrier can have a blood strikethrough ratio of 1.0 or less according to ASTM test method 22.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein, the term "nonwoven web" refers to a web having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. The basis weight of nonwoven fabrics is usually expressed in ounces of material per square yard (osy) or grams per square meter (gsm) and the fibers diameters are usually expressed in microns. (Note that to convert from osy to gsm, multiply osy by 33.91).

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. No. 4,789,699 to Kieffer et al., U.S. Pat. No. 4,781,966 to Taylor, U.S. Pat. No. 4,657,802 to Morman, and U.S. Pat. No. 4,655,760 to Morman et al., all of which are incorporated herein by reference thereto.

As used herein, the term "texturized" refers to a base web having projections from a surface of the web in the Z-direction. The projections can have a length, for instance, from about 0.1 mm to about 25 mm, particularly from about 0.1 mm to about 5 mm, and more particularly from about 0.1 mm to about 3 mm. The projections can take on many forms and can be, for instance, bristles, tufts, loop structures such as the loops used in hook and loop attachment structures, and the like. The present invention is generally directed to a finger glove that can fit over a finger. A finger glove of the present invention is generally formed from a base web material that is shaped into a glove. Further, the glove can contain a pocket for the insertion of a finger.

SUMMARY

The present invention is generally directed to an appendage sleeve that can fit onto a finger or toe to treat various ailments. An appendage sleeve of the present invention is generally formed from a base web material that is shaped into a sleeve. Further, the sleeve can contain a pocket for the insertion of a finger or toe.

In accordance with the present invention, any material commonly used in the art to manufacture cloths can be used as the base web. In particular, a base web of the present invention is typically made from a nonwoven web. More particularly, a base web of the present invention can be made from pulp fibers, synthetic fibers, thermomechanical pulp, or mixtures thereof such that the web has cloth-like properties. For instance, the base web can be made from various types of fibers, including meltblown, spunbond, bonded carded bicomponent, and crimped fibers. Moreover, the base web can also include various other materials such as elastomeric components. Various laminates, such as elastic laminates and film laminates, can also be used in the base web. For instance, suitable elastic laminates can include stretch-bonded and neck-bonded laminates.

In general, an appendage sleeve of the present invention can also have various structures. For instance, in one embodiment, the appendage sleeve can have a unitary structure. Moreover, in some embodiments, the appendage sleeve can be formed from multiple sections. Further, the sleeve can also be tapered such it can better fit onto the desired appendage.

Moreover, in some embodiments, the appendage sleeve can also include a moisture barrier that is incorporated into or applied as a layer to the base web. In general, a moisture barrier refers to any barrier, layer or film that is relatively liquid-impervious. In particular, the moisture barrier of the present invention can prevent the flow of liquid through the appendage sleeve so that a finger or toe inserted therein remains dry when the sleeve is being used. In some embodiments, the moisture barrier can remain breathable, i.e., permeable to vapors, such that an appendage within the sleeve is more comfortable. Examples of suitable moisture barriers can include films, fibrous materials, laminates, and the like.

In accordance with the present invention, various additives can also be applied, if desired, to the appendage sleeve before use. When used as a sleeve for wounds, cuts, bruises, blisters, dry skin, etc., for example, an appendage sleeve of the present invention can generally include additives such as antibiotics, anti-microbial agents, anti-inflammatory agents, NEOSPORIN, moisturizing agents, cationic polymers, and the like. In addition, when used as a sleeve for treating other ailments, such as arthritis; "black toe", "trigger finger"; or jammed, sprained, hyper-extended, dislocated, or broken appendages, an appendage sleeve of the present invention can generally include various other additives, such as topical analgesics (e.g. BEN-GAY), anti-inflammatory agents, vasodilators, corticosteroids, dimethyl sulfoxide (DMSO), capsaicin, menthol, methyl salicylate, DMSO/capsaicin, cationic polymers, anti-fungal agents, and the like.

Additives can be applied to a sleeve of the present invention in the form of an aqueous solution, non-aqueous solution (e.g., oil), lotions, creams, suspensions, gels, etc. When utilized, the aqueous solution can, for example, be coated, sprayed, saturated, or impregnated into the sleeve. In some embodiments, the additives can be applied asymmetrically. Moreover, in some instances, it may be desired that the additives comprise less than about 100% by weight of the sleeve, and in some embodiments, less than about 50% by weight of the sleeve and particularly less than 10% by weight of the sleeve.

It should be noted that any given range presented herein in intended to include any and all lesser included ranges. For example, a range from 45 to 90 would also include 50 to 90; 45 to 80; 46–89 and the like. Thus, the range of 95% to 99.99% also includes, for example, the ranges of 96% to 99.1%, 96.3% to 99.7%. and 99.1% to 99.99%. Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
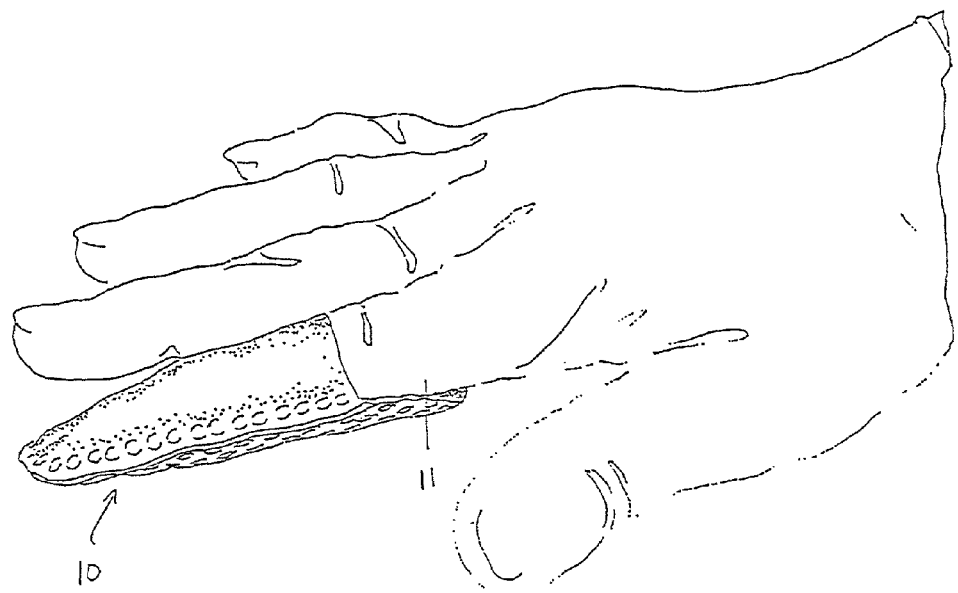
FIG. 1 is a perspective view of an appendage sleeve according to one embodiment of the present invention.

Repeat use of reference characters in the present specification and drawings is intended to represent the same or analogous features or elements of the invention.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention.

For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to a sleeve that can be used to treat various appendage ailments. In particular, the present invention is directed to an appendage sleeve that fits onto a human finger or toe.

Appendage sleeves made in accordance with the present invention are generally constructed from disposable materials, such as non-woven webs made from synthetic and/or pulp fibers. The appendage sleeve of the present invention typically includes an elastic component for providing the sleeve with form-fitting properties. For instance, it has been discovered that by forming an appendage sleeve with an elastic component in accordance with the present invention, the resulting sleeve can snuggly fit onto a person's finger or toe so that the sleeve can more effectively remain thereon. Moreover, an appendage sleeve of the present invention can remain "breathable" to aid in a person's comfort during use, while also remaining capable of substantially inhibiting the transfer of liquids from the outer surface of the sleeve to the person's finger or toe. In addition, an appendage sleeve of the present invention can also deliver an active additive for therapeutic purposes.

An appendage sleeve of the present invention can be generally formed in a variety of ways. For instance, in one embodiment, the appendage sleeve can be formed as a unitary structure from a particular base web material, such as an elastomeric nonwoven base web material. Moreover, in another embodiment of the present invention, the appendage sleeve can be formed from two or more sections of base web material. Each section can be identical or different, depending on the desired characteristics of the appendage sleeve. For example, in one embodiment, the appendage sleeve is formed from two non-identical sections, wherein one section is formed from a nonwoven material and the other section is formed from an elastomeric nonwoven material.

Referring to FIGS. 1–8, various embodiments of an appendage sleeve made in accordance with the present invention are depicted. For illustrative purposes, an appendage sleeve of the present invention is depicted and described herein as a finger sleeve. However, it should be understood that an appendage sleeve of the present invention is not limited to finger sleeves, and that any reference to a finger sleeve herein can also apply to toe sleeves. In particular, a toe sleeve of the present invention is essentially identical to a finger sleeve of the present invention, except that the shape of the toe sleeve can slightly differ from a finger sleeve to better fit the contours of the toe. Moreover, although the finger sleeve is depicted as covering one finger, it should be understood that an appendage sleeve of the present invention can also be made such that two, three, four, or five fingers or toes can be inserted therein.

Figure 8:
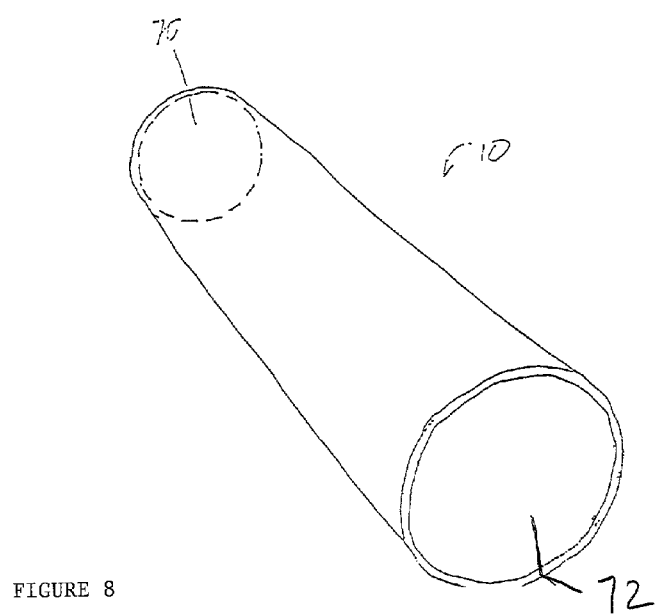
FIG. 8 is a perspective view of a tapered appendage sleeve having two open ends according to one embodiment of the present invention.

In this regard, as shown in FIG. 8, one embodiment of the present invention includes a finger sleeve 10 that can be formed as a unitary structure from a single piece of fabric. In this embodiment, the sleeve 10 has two open ends 70 and 72 such that a finger can be inserted into one end and through the other end. Once on a finger, the sleeve 10 can be maneuvered by a user until the sleeve is positioned to cover a certain wound or joint. Moreover, the length of the appendage finger sleeve 10 can vary depending on the application. For example, in one embodiment, the sleeve 10 can have a length between about 0.8 centimeters to about 5 centimeters.

In some embodiments, as shown in FIG. 8, the sleeve 10 can also have a slightly tapered shape such that an end 70 is narrower than an end 72. Such a tapered shape can allow the sleeve 10 to better conform to the contours of a finger or toe. However, it should be understood that such a tapered shape is not required, and that any other shape can be utilized in the present invention as long as a toe or finger can be inserted into the sleeve 10. In addition, the sleeve 10 can also be tapered in a manner such that the center portion of the sleeve 10 has a slightly greater width than ends 70 and 72. By providing a center portion with a greater width (not shown), the sleeve 10 may better fit over the knuckle or joint of a finger or toe.

Referring to FIGS. 1–7, other embodiments of an appendage sleeve of the present invention are depicted. In each of these embodiments, the finger sleeve 10 includes one open end 72 and a closed end 70 for the insertion of a finger. The closed end, in these embodiments, can be particularly useful for treating a wound or ailment at the tip of a finger or toe. It should be understood, however, that although one open end is depicted in FIGS. 1–7, two open ends are equally suitable and may be desired in certain applications.

Figure 4:
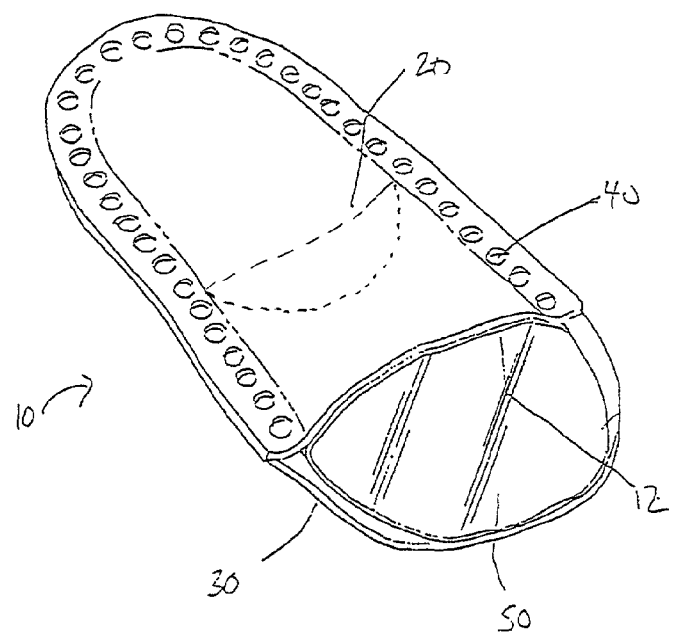
FIG. 4 is a perspective view of the two-sided appendage sleeve of FIG. 3.
Figure 5:
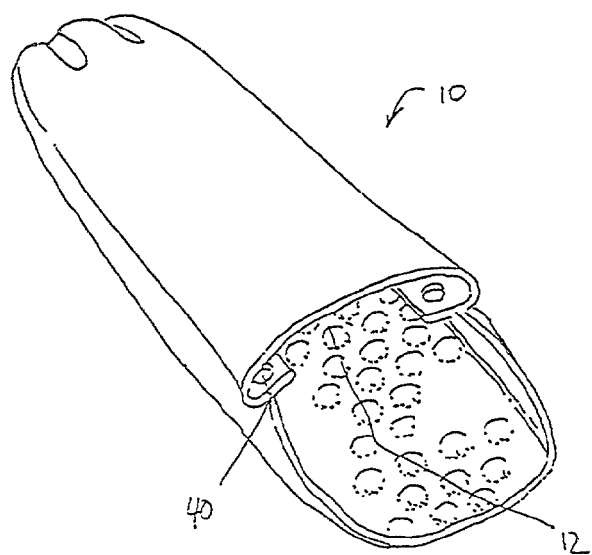
FIG. 5 is a perspective view of an appendage sleeve turned "inside-out" according to one embodiment of the present invention.
Figure 6:
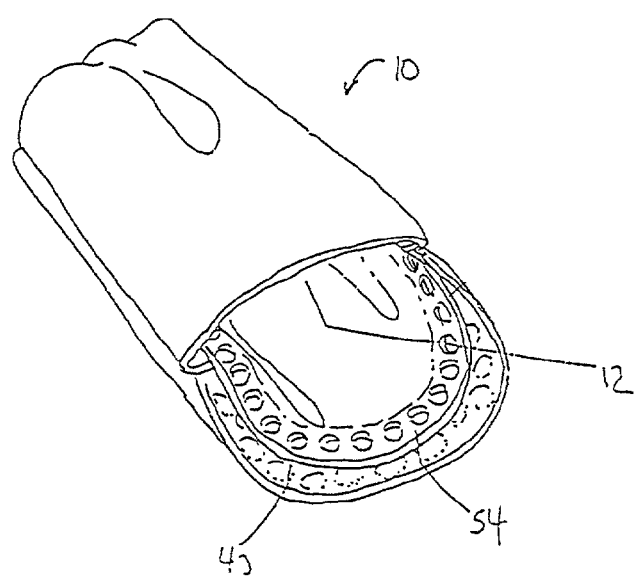
FIG. 6 is a perspective view of an appendage sleeve turned "inside-out" according to another embodiment of the present invention.

As shown in FIGS. 4–6, the finger sleeve 10 can also include a first section 20 and a second section 30. Generally, one section of the finger sleeve 10 can be bonded or attached to the other half in a finger pattern by any manner known in the art, such as by adhesive, thermal or mechanical bonding, such that the connection of the sections can form an open end 72 for the insertion of a finger. In the embodiment depicted in FIG. 4, for example, the first section 20 is attached in a finger pattern to the second section 30 at their respective outer edges via the seams 40 to form a finger sleeve 10 having an open end 72. Once each section is bonded or attached at seams 40, the materials forming each of the sections 20 and 30 can then be cut adjacent to the seams such that a finger-shaped sleeve 10 is formed.

In one embodiment of the present invention, in order to soften the feel of the seams of the finger sleeve during use, a plurality of cuts can be made along the edges of the seam. The cuts, which can be referred to as microcuts, can be narrowly spaced along the seam. The cuts can be, for instance, less than 1 cm apart, particularly less than about 0.5 cm apart, and more particularly, less than about 1 mm apart. The cuts can extend substantially the entire width of the seam. For instance, the length of the cuts can be from about 0.1 cm to about 0.5 in length depending upon the particular application.

The microcuts can be formed into the seam using any suitable process. For instance, the cuts can be made using cutting dyes, laser technology, ultrasonic knives, and the like.

In some embodiments, as depicted in FIGS. 5–6, the sleeve 10 can also be turned inside-out such that the seams 40 are located inside the pocket 12. For example, as shown in FIG. 6, the seams 40 of the sleeve wipe 10 can be pushed into the pocket 12 such that the seams 40 remain on the inside of the sleeve 10, as depicted in FIG. 5. This "inside-out" position, as shown in FIG. 5, can provide a sleeve with improved aesthetics. Moreover, the seams can also provide a better fit by providing more friction to the appendage. In addition, in some embodiments, this "inside-out" position can enable sleeve 10 to be more resistant to "flattening out" during use.

As shown in FIGS. 1–4, the first section 20 can also, in some embodiments, have a length greater than the second section 30 such that the first section 20 includes a portion (or pull-on tab) 26 that extends beyond the edge of the second section 30. By extending beyond the second section 30, the portion 26 can facilitate placement of a finger sleeve 10 over a finger. In particular, a user can conveniently grab the portion 26 to place a finger sleeve 10 over a finger 11. Further, in another embodiment, a pull-on tab 26 can also be provided in the middle portion of the finger sleeve 10 such that a user can then pull tab 26 in a direction perpendicular to the lengthwise direction of a flattened finger sleeve. As a result, the tab 26 can facilitate the insertion of a finger into a sleeve 10 by "spreading out" the sleeve in an upwardly direction as a finger is inserted therein. The tab 26 can also help to prevent contamination of the internal surface of the appendage sleeve that is to contact an open wound. In particular, the tab 26 can prevent the undesirable "rubbing off" of certain delivery agents that are applied to the appendage sleeve by allowing the internal surface of the sleeve to be raised above the skin or wound during insertion.

In general, the appendage sleeve of the present invention, such as depicted in FIGS. 1–8, can be formed from a variety of materials. For instance, as stated above, the appendage sleeve can be formed as a unitary structure from a base web. In another embodiment, the appendage sleeve can be formed from two sections made from the same or different base webs. It should be understood, however, that, as used herein, a base web of the present invention is meant to include one or more layers of fibrous materials.

For most applications, appendage sleeves made in accordance with the present invention are constructed for nonwoven webs containing an elastic component referred to herein as an "elastic nonwoven." An elastic nonwoven is a nonwoven material having non-elastic and elastic components or having purely elastic components.

The elastic component, for instance, can form a separate section of the appendage sleeve. For example, the appendage sleeve can be made from two or more sections of material that includes a first section made from a non-elastic material and a second section made from an elastic material. Alternatively, the appendage sleeve can be made from a single piece of material that contains an elastic component. For example, in this embodiment, the elastic component can be a film, strands, non-woven webs or elastic filament incorporated into a laminate structure.

Non-elastic materials used in the present invention typically include nonwoven webs or films. The nonwoven webs, for instance, can be meltblown webs, spunbond webs, carded webs and the like. The webs can be made from various fibers, such as synthetic or natural fibers. For instance, in one embodiment, synthetic fibers such as fibers made from thermoplastic polymers, can be used to construct the appendage sleeve of the present invention. For example, suitable fibers could include melt-spun filaments, staple fibers, melt-spun multicomponent filaments, and the like.

Synthetic fibers or filaments used in making the non-woven materials of the base web have any suitable morphology that may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof. As used herein, the term "blend" means a mixture of two or more polymers. Furthermore, unless otherwise specifically limited, the term "polymer" shall include all possible geometrical configurations of the molecule. These configurations include, but are not limited to, isotatic, synditatic, and random symmetries.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers and the like.

Many polyolefins are available for fiber production, for example polyethylenes such as Dow Chemical's PE XU 61800.41 linear low density polyethylene ("LLDPE") and 25355 and 12350 high density polyethylene ("HDPE") are such suitable polymers. Fiber-forming polypropylenes include Exxon Chemical Company's Escorene7 PD 3445 polypropylene and Montell Chemical Co.'s PF-304 and PF-015. Many other conventional polyolefins are commercially available and include polybutylenes and others.

Examples of polyamides and their methods of synthesis may be found in "Polymer Resins" by Don E. Floyd (Library of Congress Catalog No. 66-20811, Reinhold Publishing, New York, 1966). Particularly commercially useful polyamides are nylon-6, nylon 6,6, nylon-11 and nylon-12. These polyamides are available from a number of sources such as Emser Industries of Sumter, S.C. (Grilon7 & Grilamid7 nylons), Atochem Inc. Polymers Division of Glen Rock, N.J. (Rilsan7 nylons), Nyltech of Manchester, N.H. (grade 2169, Nylon 6), and Custom Resins of Henderson, Ky. (Nylene 401-D), among others.

As stated above, synthetic fibers added to the base web can also include staple fibers which are added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. For instance, staple fibers typically have fiber lengths of 5 mm and greater. Staple fibers can increase the strength and softness of the final product.

The fibers used in a base web of the present invention can also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the z-direction as well as increase web strength properties.

The synthetic fibers added to the base web can also include bicomponent fibers. Bicomponent fibers are fibers that can contain two materials such as but not limited to in a side by side arrangement, in a matrix-fibril arrangement, wherein a core polymer has a complex cross-sectional shape, or in a core and sheath arrangement. In a core and sheath fiber, generally the sheath polymer has a lower melting temperature than the core polymer to facilitate thermal bonding of the fibers. For instance, the core polymer, in one embodiment, can be nylon or a polyester, while the sheath polymer can be a polyolefin such as polyethylene or polypropylene. Such commercially available bicomponent fibers include "CELBOND" fibers marketed by the Hoechst Celanese Company.

Besides or in addition to synthetic fibers, pulp fibers can also be used to construct the appendage sleeve of the present invention. The pulp fibers used in forming the base web may be soft wood fibers having an average fiber length of greater than 1 mm, and particularly from about 2 to 5 mm based on a length weighted average. Such fibers can include northern softwood craft fibers, redwood fibers, and pine fibers. Secondary fibers obtained from recycled materials may also be used. In addition, hardwood pulp fibers, such as eucalyptus fibers, can also be utilized in the present invention.

Besides the above-mentioned fibers, thermomechanical pulp fibers can also be added to the base web. Thermomechanical pulp, as is known to one skilled in the art, refers to pulp that is not cooked during the pulping process to a lesser extent than conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, thermomechanical pulp can be added to a layer of the base web in an amount from about 10% to about 30% by weight of the fibers contained in the layer. When using thermomechanical pulp, a wetting agent is also preferably added during formation of the web. The wetting agent can be added in an amount less than about 1% by weight of the fibers and, in one embodiment, can be a sulphonated glycol.

When pulp fibers are used to form the base web, the web can be treated with a chemical debonding agent to reduce inner fiber-to-fiber strength. Suitable debonding agents that may be used in the present invention when the base web contains pulp fibers include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun, which is incorporated herein by reference. In one embodiment, the debonding agent can be an organic quaternary ammonium chloride. In this embodiment, the debonding agent can be added to the fiber slurry in an amount from about 0.1% to about 1% by weight, based on the total weight of fibers present within the furnish.

Moreover, in some embodiments of the present invention, a base web of the present invention can also be hydraulically entangled (or hydroentangled) to provide further strength. Hydroentangled webs, which are also known as spunlace webs, refer to webs that have been subjected to columnar jets of a fluid that cause the fibers in the web to entangle. Hydroentangling a web typically increases the strength of the web. Thus, according to the present invention, in order to increase the strength of a web, a base web of the present invention can be hydroentangled. For example, in one embodiment, the base web can comprise HYDROKNIT7, a nonwoven composite fabric that contains 70% by weight pulp fibers that are hydraulically entangled into a continuous filament material. HYDROKNIT7 material is commercially available from Kimberly-Clark Corporation of Neenah, Wisconsin. Hydraulic entangling may be accomplished utilizing conventional hydraulic entangling equipment, such as may be found in, for example, in U.S. Pat. No. 3,485,706 to Evans or U.S. Pat. No. 5,389,202 to Everhart, et al., the disclosures of which are hereby incorporated by reference.

As mentioned above, for most application, non-woven webs used to construct the appendage sleeve will contain synthetic fibers. For non-woven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al., which is incorporated herein by reference. In addition, other conventional means of bonding, such as oven bonding, ultrasonic bonding, hydroentangling, are combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less.

More specifically, the bond areas of the present inventive webs can be in the range of 40% total bond area or less. Even more specifically, the bond areas can be in the range of 30% total bond area or less and may be in the range of about 15% total bond area or less. Typically, a bond area of at least about 10% can be acceptable for creating the base webs of the present invention, although other total bond areas will fall within the scope of the invention, depending on the particular characteristics desired in the final product. Stated generally, the lower limit on the percent bond area suitable for forming the nonwoven material of the present invention is the point at which fiber pull-out excessively reduces the surface integrity and durability of the material. The percent bond areas will be affected by a number of factors, including the type(s) of polymeric materials used in forming the fibers or filaments of the nonwoven web, whether the nonwoven web is a single- or multi-layer fibrous structure, and the like. Bond areas ranging from about 15% to about 50% have been found suitable for point unbonded webs while bond areas ranging from 1% to 50% have been found suitable for point bonded webs.

As described above, besides containing various non-elastic materials, the appendage sleeve of the present invention can also contain an elastomeric component.

By containing such an elastomeric component, the appendage sleeve of the present invention can better fit around a human finger or toe.

Figure 2:
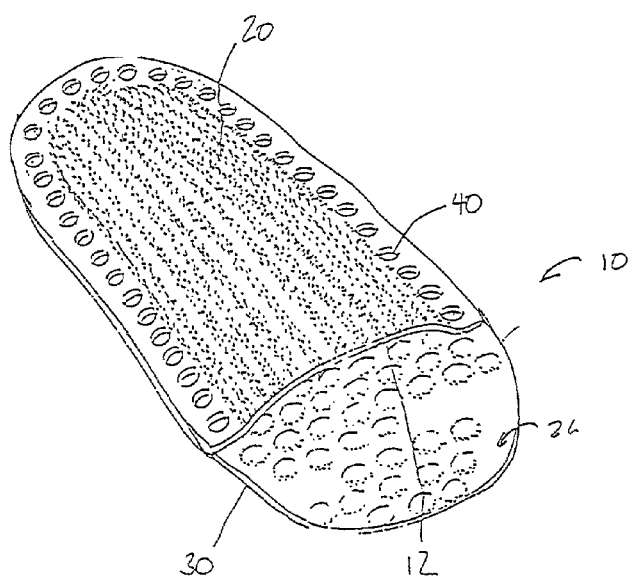
FIG. 2 is a perspective view of a two-sided appendage sleeve according to one embodiment of the present invention.
Figure 3:
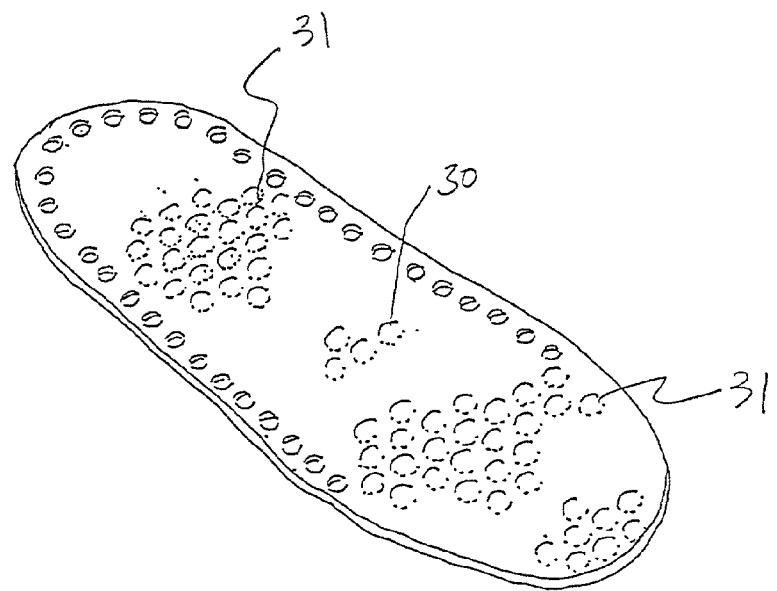
FIG. 3 is a perspective view of a bottom section of a two-sided appendage sleeve according to one embodiment of the present invention.
Figure 7:
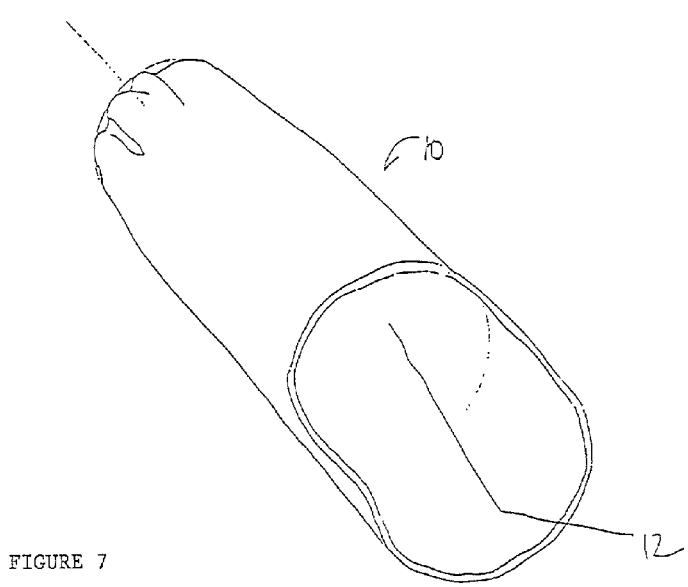
FIG. 7 is a perspective view of an embodiment of an appendage sleeve having a unitary structure.

In this regard, referring to FIGS. 7 & 8, one embodiment of the present invention is depicted that includes an appendage sleeve made from a base web having at least one elastomeric component. In particular, the finger sleeve 10 can be formed into a unitary structure from a base web that includes an elastomeric material. Moreover, in other embodiments, such as shown in FIG. 2, one section 20 of the finger sleeve 10 can include an elastomeric component.

When present in the appendage sleeve, the elastomeric component can take on various forms. For example, the elastomeric component can be elastic strands or sections uniformly or randomly distributed throughout the base web. Alternatively, the elastomeric component can be an elastic film or an elastic non-woven web. The elastomeric component can also be a single layer or a multi layered material.

In general, any material known in the art to possess elastomeric characteristics can be used in the present invention as an elastomeric component. Useful elastomeric materials can include, but are not limited to, films, foams, nonwoven materials, etc. For example, suitable elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers for the A and A' blocks, and the present block copolymers are intended to embrace linear, branched and radial block copolymers. In this regard, the radial block copolymers may be designated (A-B)m-X, wherein X is a polyfunctional atom or molecule and in which each (A-B)m-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer," and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks.

The elastomeric component may be formed from, for example, elastomeric (polystyrene/poly(ethylene-butylene)/polystyrene) block copolymers. Commercial examples of such elastomeric copolymers are, for example, those known as KRATON7 materials which are available from Shell chemical Company of Houston, Tex. KRATON7 block copolymers are available in several different formulations, a number of which are identified in U.S. Pat. Nos. 4,663,220, 4,323,534, 4,834,738, 5,093,422 and 5,304,599, which are incorporated herein by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from the Shell chemical Company of Houston, Tex. under the trade designation KRATON7 G-1657.

Other exemplary elastomeric materials which may be used include polyurethane elastomeric materials such as, for example, those available under the trademark ESTANE7 from B.F. Goodrich & Co. or MORTHANE7 from Morton Thiokol Corp., polyester elastomeric materials such as, for example, those available under the trade designation HYTREL7 from E.I. DuPont De Nemours & Company, and those known as ARNITEL7, formerly available from Akzo Plastics of Amhem, Holland and now available from DSM of Sittard, Holland.

Another suitable material is a polyester block amide copolymer having the formula:

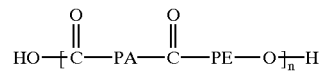

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX7 from ELF Atochem Inc. of Glen Rock, N.J. Examples of the use of such polymers may be found in U.S. Pat. Nos. 4,724,184, 4,820,572 and 4,923,742 to Killian.

Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

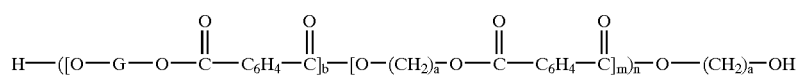

where "G" is selected from the group consisting of poly(oxyethylene)-alpha,omega-diol, poly(oxypropylene)-alpha,omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL7, formerly available from Akzo Plastics of Amhem, Holland and now available from DSM of Sittard, Holland, or those known as HYTREL7 which are available from E.I. DuPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs.

Elastomeric olefin polymers are available from Exxon Chemical Company of Baytown, Tex. under the trade name ACHIEVE7 for polypropylene based polymers and EXACT7 and EXCEED7 for polyethylene based polymers. Dow Chemical Company of Midland, Mich. has polymers commercially available under the name ENGAGE7. Exxon generally refers to their metallocene catalyst technology as "single site" catalysts while Dow refers to theirs as "constrained geometry" catalysts under the name INSIGHT7 to distinguish them from traditional Ziegler-Natta catalysts which have multiple reaction sites.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck bonded laminates.

The elastic member used in neck bonded materials, stretch-bonded materials, stretch-bonded laminates, neck bonded laminates and in other similar laminates can be made from materials, such as described above, that are formed into films, such as a microporous film, fibrous webs, such as a web made from meltblown fibers, or foams. A film, for example, can be formed by extruding a filled elastomeric polymer and subsequently stretching it to render it microporous.

Fibrous elastic webs can also be formed from an extruded polymer. For instance, as stated above, in one embodiment the fibrous web can contain meltblown fibers. The fibers can be continuous or discontinuous. Meltblown fabrics have been conventionally made by extruding a thermoplastic polymeric material through a die to form fibers. As the molten polymer fibers exit the die, a high pressure fluid, such as heated air or steam, attenuates the molten polymer filaments to form fine fibers. Surrounding cool air is induced into the hot air stream to cool and solidify the fibers. The fibers are then randomly deposited onto a foraminous surface to form a web. The web has integrity but may be additionally bonded if desired.

Besides meltblown webs, however, it should be understood that other fibrous webs can be used in accordance with the present invention. For instance, in an alternative embodiment, elastic spunbond webs can also be formed. Spunbond webs are typically produced by heating a thermoplastic polymeric resin to at least its softening temperature, then extruding it through a spinnerette to form continuous fibers, which can be subsequently fed through a fiber draw unit. From the fiber draw unit the fibers are spread onto a foraminous surface where they are formed into a web and then bonded such as by chemical, thermal or ultrasonic means.

In one embodiment, the elastic member can be a necked stretched bonded laminate. As used herein, a necked stretched bonded laminate is defined as a laminate made from the combination of a necked bonded laminate and a stretch-bonded laminate. Examples of necked stretched bonded laminates are disclosed in U.S. Pat. Nos. 5,114,781 and 5,116,662, which are both incorporated herein by reference. Of particular advantage, a necked stretched bonded laminate is stretchable in a machine direction and a cross machine direction.

Besides including a non-elastic component or an elastic component, the appendage sleeve of the present invention can further include a moisture barrier that is incorporated into or laminated to a base web of the present invention. The moisture barrier can be a liquid-impervious layer or a liquid absorbent layer.

Such a barrier can prevent, or at least minimize, leakage from outside the sleeve by establishing a barrier to the passage of liquid from the sleeve to the finger placed therein. For example, as shown in FIG. 4, a layer of material or film can be provided to form the moisture barrier 50, which can act as a barrier between the outer layer of a finger sleeve 10 and a finger. Moreover, in this embodiment, the moisture barrier 50 can act as an inner lining for the second section 30 only, while the first section 20 possesses no such inner lining. However, it should also be understood that the moisture barrier 50 may be a liner for both the first section 20 and the second section 30. Moreover, the moisture barrier 50 can be applied asymetrically or unevenly to the sleeve 10 such that one portion of the sleeve is substantially moisture-impervious, while another portion is not. It should be understood that the moisture barrier 50 can be applied to the sleeve 10 as a layer of the base web, or as an outer lining for the base web. Moreover, it should also be understood that the moisture barrier can be inherent within the base web structure such that it would not constitute a separate lining thereof.

In one embodiment of the present invention, the moisture barrier 50 can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the sleeve to the finger, the use of such liquid- and vapor-impermeable barriers can sometimes result in a relatively uncomfortable level of humidity being maintained in the sleeve 10.

As such, in some embodiments, breathable, liquid-impermeable barriers are desired. For instance some suitable breathable, liquid-impermeable barriers can include barriers such as disclosed in U.S. Pat. No. 4,828,556 to Braun et al., which is incorporated herein in its entirety by reference. The breathable barrier of Braun et al. is a multi layered, cloth like barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids which connect the upper and lower surfaces of the film.

In other cases, various breathable films can be constructed with micropores to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker et al. The fabric material described in Junker et al. comprises a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Although the inventors do not intend to be held to a particular mechanism of operation, it is believed that films made from such polymers solubilize water molecules and allow transportation of those molecules from one surface of the film to the other.

Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Moisture barrier layers, as described above, can be used alone or incorporated into a laminate when used to construct the appendage sleeve of the present invention. When incorporated into a laminate, the laminate can include various non-woven webs in combination with the moisture barrier layer. For instance, moisture barrier laminates can be formed from many processes such as for example, meltblown processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate moisture barrier of the present invention is a spunbond/meltblown/spunbond (SMS) and/or spunbond/meltblown (SM) material. An SMS material is described in U.S. Pat. No. 4,041,203 to Brock et al. which is incorporated herein in its entirety by reference. Other SMS products and processes are described for example in U.S. Pat. No. 5,464,688 to Timmons et al., U.S. Pat. No. 5,169,706 to Collier et al. and U.S. Pat. No. 4,766,029 to Brock et al., all of which are also incorporated herein in their entireties by reference. Generally, an SMS material will consist of a meltblown web sandwiched between two exterior spunbond webs. Such SMS laminates are available from Kimberly-Clark Corporation under marks such as Spunguard7 and Evolution7. The spunbonded layers on the SMS laminates provide durability and the internal meltblown barrier layer provides porosity and additional cloth like feel. Similar to an SMS laminate, an SM laminate is a spunbond layer laminated to a meltblown layer.

In forming an appendage sleeve of the present invention with a moisture barrier, the barrier can be bonded together with the other layers of the sleeve in a number of various ways. Thermal bonding, adhesive bonding, ultrasonic bonding, extrusion coating, and the like, are merely examples of various bonding techniques that may be utilized in the present process to attach the moisture barrier to the fibrous layers of the appendage sleeve.

In some embodiments, any of the above layers and/or materials can also be dyed or colored so as to form a base web or moisture barrier having a particular color. For example, in one embodiment, the moisture barrier 50 can be provided with a colored background. For instance, white tufts, colored tufts, and/or a white titanium oxide background could be utilized.

As described above, the appendage sleeve of the present invention can be made from various components and contain various features. For instance, the appendage sleeve can include a non-elastic component, an elastic component, and a moisture barrier. Further, the appendage sleeve can be made from single layer material or laminates which, in turn, can be made from various materials and fibers. One particular embodiment of the appendage sleeve made in accordance with the present invention will now be discussed. Specifically, the embodiment discussed below is constructed similar to the embodiment illustrated in FIG. 2, except that the appendage sleeve includes two open ends, such as shown in FIG. 8.

In this embodiment, the appendage sleeve includes the first section 20 thermally bonded to the second section 30. In this embodiment, the second section 30 is a three layer laminate. The laminate includes an interior polypropylene spunbond layer, a middle moisture barrier layer, and an outer bicomponent spunbond layer that forms an exterior surface of the appendage sleeve.

The polypropylene spunbond layers made from spunbond polypropylene filaments can have a basis weight of from about 0.3 osy to about 1.0 osy, and can particularly have a basis weight of about 0.5 osy. The moisture barrier layer, on the other hand, can be a film made from linear low-density polyethylene containing a calcium carbonate filler. The film can be stretched in order to create pores for making the film breathable while remaining substantially impermeable to liquids. The moisture barrier layer can have a basis weight from about 0.2 osy to about 1.0 osy, and particularly can have a basis weight of about 0.5 osy. The polypropylene spunbond layer can be adhesively secured to the moisture barrier layer.

In an alternative embodiment, the interior polypropylene spunbond layer can be replaced with a nonwoven web made from polypropylene/polyethylene bicomponent fibers. The middle moisture barrier layer, on the other hand, can be a film made from a mixture of polymers, such as CATALLOY film marketed by the Pliant Corporation.

The exterior layer can be a spunbond or through air bonded web made from bicomponent polyethylene/polypropylene filaments in a side-by-side arrangement. The exterior layer can have a basis weight of from about 1.0 osy to about 5.0 osy, and can particularly have a basis weight of from about 2.0 osy to about 4.0 osy. Alternatively, the exterior layer itself can be a layered or laminate structure. For example, a two-banked process can be used in which a layer of larger diameter fibers is formed on a layer of small diameter fibers.

The exterior bicomponent spunbond layer can be laminated to other layers using a thermal point bonding process, such as a point unbonded pattern process.

The first section 20 is an elastic laminate. For instance, the first section 20 can be a stretch-bonded laminate sheet. The stretch-bonded laminate sheet can include elastic threads made from an elastomeric material sandwiched between two polypropylene spunbond layers. The elastic threads can be, for instance, made from a styrene-ethylene butuylene-styrene copolymer, such as KRATON G2740 available from the Shell Chemical Company. The stretch-bonded laminate can have a basis weight of from about 1.0 osy to about 5 osy, particularly from about 1.5 osy to about 2.5 osy, and more particularly from about 2.0 osy to about 3.0 osy.

Instead of a stretch bonded laminate sheet, the first section 20 can also be a neck bonded laminate sheet. The neck bonded laminate sheet can include a metallocene catalyzed elastic polyethylene film sandwiched between two polypropylene spunbond layers. The spunbond layers can have a basis weight of about 0.45 osy prior to being stretched. The polyethylene film, on the other hand, can have a basis weight from about 0.5 osy to about 1.5 osy.

The first section 20 can be attached with the second section using various methods. For example, as shown in FIG. 2, the first section 20 can be attached to the second section 30 using ultrasonic bonding. For example, as shown in FIG. 2, the first section 20 can be ultrasonically bonded to the second section 30 along the outer edges in order to form a pocket for the insertion of a finger.

Once the first section 20 and the second section 30 are bonded together, excess material can be cut and removed from the appendage sleeve. In general, any suitable cutting method can be used in order to trim away excess material. For example, the material can be cut using a high pressure jet of water referred to as a water knife or can be cut using a conventional mechanical device, such as a cutter or a pair of shears. In one embodiment, the first section 20 and the second section 30 can be simultaneously bonded together and cut from the materials from which they are made. For instance, ultrasonic energy can be used to bond and cut materials in one step.

The dimensions of the appendage sleeve that is formed in accordance with the present invention will depend upon the particular application and purpose for which the appendage sleeve is to be used. For instance, the appendage sleeve can be constructed in order to fit around the finger of an adult or the finger of a child. Further, the appendage sleeve can also be constructed to fit around two fingers. For most single finger appendage sleeves, the sleeve should have a length of from about 1 inch to about 5 inches and a median flattened width of from about 0.5 inches to about 1.5 inches. When constructed to fit around two fingers, the appendage sleeve can have a median width of from about 0.75 inches to about 2.5 inches, depending on the elasticity of the sleeve.

In order to provide therapeutic benefits to a finger or toe, a variety of chemicals can be applied to the appendage sleeve of the present invention. When used as a sleeve for wounds, cuts, bruises, blisters, dry skin, etc., for example, an appendage sleeve of the present invention can generally include any additive commonly used as healing or pain-killing agents, particularly those which are currently used on conventional appendage bandages. Examples of such additives can include, but are not limited to, antibiotics, anti-microbial agents, anti-inflammatory agents, neosporin, moisturizing agents, cationic polymers, and the like.

For instance, cationic polymers can help clean wounds because they typically have a strong attraction for negatively charged bacteria and deleterious acidic byproducts. One example of a cationic polymer that is suitable for use in the present invention is chitosan (poly-N-acetylglucosamine, a derivative of chitin) or chitosan salts. Chitosan and its salts are natural biopolymers that can have both hemostatic and bacteriostatic properties. As a result, chitosan can help reduce bleeding and infection. In addition to chitosan and chitosan salts, any other cationic polymers, such as cationic starches (e.g. COBOND made by National Starch) or oligomeric compounds can be used. In some embodiments, combinations of cationic materials can be utilized. In addition, when used as a sleeve for treating other ailments, such as arthritis; "black toe", "trigger finger"; or jammed, sprained, hyper-extended, dislocated, or broken appendages, an appendage sleeve of the present invention can generally include any additive commonly used to treat such ailments. Examples of such additives can include, but are not limited to, topical analgesics (e.g. BEN-GAY), anti-inflammatory agents, vasodilators, corticosteroids, dimethyl sulfoxide (DMSO), capsaicin, menthol, methyl salicylate, DMSO/capsaicin, cationic polymers, anti-fungal agents, and the like. For instance, suitable anti-inflammatory agents can include any cyclooxygenase-1 (COX-1) or cyclooxygenase-2 (COX-2) inhibitors.

In general, the chemical additives described above can be applied to an appendage sleeve of the present invention according to a number of ways known in the art. For example, the additives can be applied to the sleeve using a saturant system, such as disclosed in U.S. Pat. No. 5,486,381 to Cleveland et al., which is incorporated herein by reference. Moreover, the additives can also be applied by various other methods, such as print, blade, roll, spray, spray-drying, foam, brush treating applications, etc., which are well known in the art. The additives can further be applied as a mixture of molten solids or co-extruded onto the sleeve. Additionally, in another embodiment, the chemical additives can be impregnated into the material during manufacturing as is well known in the art. It should be understood that when coated onto a sleeve as described above, the additives can be applied to the base web before or after the base web is stamped or bonded to form an appendage sleeve of the present invention. Furthermore, if desired, it should also be understood that various additives, solutions, and chemicals can be applied by the consumer to the appendage sleeve just before use.

In another embodiment, the additive is encapsulated and then applied to the dental wipe. Encapsulation is a process by which a material or mixture of materials is coated with or entrapped within another material or mixture of materials. The technique is commonly used in the food and pharmaceutical industries. The material that is coated or entrapped is normally a liquid, although it can also be a solid or gas, and is referred to herein as the core material. The material that forms the coating is referred to as the carrier material. A variety of encapsulation techniques are well-known in the art and can be used in the current invention, including spray drying, spray chilling and cooling, coacervation, fluidized bed coating, liposome entrapment, rotational suspension separation, and extrusion.

Spray drying is commonly used for encapsulating food and flavors. To prepare a material for spray drying, the carrier material is dissolved in an aqueous solution. The core ingredient is added to this solution and mixed thoroughly. A typical load of carrier to core material is 4:1, although much higher or lower loads can be used. The mixture is homogenized, and then fed into a spray dryer where it is atomized and released into a stream of hot air. The water is evaporated, leaving a dried particle comprising the core material trapped within the carrier matrix.

Suitable carrier materials include but are not limited to gums, gum Arabic, modified starches, gelatin, cellulose derivatives, and maltodextrins. Suitable core materials include but are not limited to flavors, natural oils, additives, sweeteners, stabilizers besides the other various additives mentioned above.

Regardless of the mechanism utilized to apply the chemical additives to the sleeve, the additives can be applied to the sleeve via an aqueous solution, non-aqueous solution, oil, lotion, cream, suspension, gel, etc. When utilized, an aqueous solution can contain any of a variety of liquids, such as various solvents and/or water. Moreover, the solution can often contain more than one additive. In some embodiments, the additives applied by an aqueous solution or otherwise constitute approximately less than 80% by weight of the appendage sleeve. In other embodiments, in order to maintain sufficient absorbency of the sleeve, the additives can be applied in an amount less than about 50% of the weight of the sleeve.

Moreover, in some embodiments, the additives can also be applied asymmetrically onto the sleeve to reduce costs and maximize performance of the sleeve. For instance, in one embodiment, a flat sheet of the base web is asymmetrically contacted with a particular coating agent, and thereafter stamped and bonded to form an appendage sleeve of the present invention, wherein only the surface that directly covers the ailing portion of the appendage is coated with the additives. In another embodiment, the appendage sleeve is stamped and bonded, and thereafter asymmetrically coated with a particular coating agent.

Prior to be shipped and sold, the appendage sleeve of the present invention can be placed in various packaging in order to preserve any additives applied to the appendage sleeve or otherwise to maintain the appendage sleeve in a sterile environment. Various packaging materials that can be used include polyvinyl alcohol films, film foil laminates, metalized films, multi-layered plastic films, and the like.

The present invention may be better understood by reference to the following examples.

EXAMPLE 1

An appendage sleeve of the present invention was formed as follows and applied with an antibiotic ointment. Specifically, a first section made from a coform base sheet was ultrasonically welded to a stretch-bonded laminate sheet using a Branson 920 IW ultrasonic welder.

The coform sheet was a meltblown web containing 50% pulp fibers and 50% by weight polypropylene fibers. The coform sheet had a basis weight of about 5 osy.

The stretch-bonded laminate sheet, on the other hand, included threads of an elastic material sandwiched between two polypropylene spunbond layers. The elastic material used was KRATON G2740 S-EB-S block copolymer available from the Shell Oil Company. The stretch-bonded laminate sheet had a basis weight of 2.5 osy. An imprinted, magnesium bond plate was used to bond the stretch-bonded laminate sheet to the coform base sheet.

The two sheets were welded together to produce a tubular structure, with straight sides and a flattened interior width of about 1.8 cm. The tubular structure was then cut to a length of 3.0 cm along the seams, with pull-on tabs on both sides.

The coform side of the finger sleeve was then treated with a triple antibiotic ointment. The antibiotic ointment comprised 100 mg of NEOSPORIN, which was obtained from Warner-Lambert Consumer Healthcare located in Morris Plains, N.J. NEOSPORIN contained the following active ingredients: polymyxin B sulfate, bacitracin zinc, and neomycin. Once applied with the ointment, the appendage sleeve was then inverted such that the seams and ointment were positioned on the inner surface of the finger sleeve. The sleeve was then pulled over a finger and used as a bandage.

EXAMPLE 2

The ability of an appendage sleeve of the present invention to be applied with the following arthritis cream was demonstrated. The appendage sleeve of Example 1 was initially formed as described above. Thereafter, the coform side of the finger sleeve was treated with an arthritis pain relief cream. The cream comprised 350 mg of CAPZASIN-P, which was obtained from Chattem, Inc., located in Chattanooga, Tenn. CAPZASIN-P contained 0.025% capsaicin as its active ingredient. Once applied with the cream, the appendage sleeve was then inverted such that the seams and cream were positioned on the inner surface of the finger sleeve. The sleeve was then pulled over a sore finger for pain relief.

EXAMPLE 3

The ability of an appendage sleeve of the present invention to be applied with the following analgesic lotion was demonstrated. The appendage sleeve of Example 1 was initially formed as described above. Thereafter, the coform side of the finger sleeve was treated with an analgesic lotion. The analgesic lotion comprised 75 mg of AURUM, which was obtained from Au Pharmaceuticals, located in Tyler, Tex. AURUM contained methyl salicylate, camphor, and menthol as its active ingredients. Once applied with the lotion, the appendage sleeve was then inverted such that the seams and lotion were positioned on the inner surface of the finger sleeve. The sleeve was then pulled over a sore finger for pain relief.

EXAMPLE 4

The ability of an appendage sleeve of the present invention to cover a paper cut on a finger was demonstrated. An appendage sleeve as described in Example 1 was constructed. In this embodiment, however, the resulting bonded sleeve was in the shape of a finger having a rounded, closed end at the top and straight sides tapering outwards, such that the width of the bond pattern 1 cm from the top was about 1.7 cm, and the interior width at 4.2 cm from the top was about 2.2 cm. Thereafter, excess material was trimmed from the edges of the sleeve and the sleeve was inverted to place the seams on the inside. The coform side of the sleeve was about 4.2 cm in length and the stretch-bonded laminate side was about 5.2 cm in length to provide a pull-on tab for aiding in placing the sleeve over a finger. The formed finger sleeve was then used to cover a paper cut on a finger.

EXAMPLE 5

The ability of an appendage sleeve of the present invention to cover an abrasion was demonstrated. Initially, the finger sleeve of Example 4 was formed. Thereafter, the top of the finger sleeve was cut off such that the sleeve had two open ends. The resulting finger sleeve had a length of 3.2 cm and was used to cover an abrasion.

EXAMPLE 6

A tubular-shaped appendage sleeve of the present invention was formed as described in Example 1. The tubular-shaped sleeve was cut at various lengths to provide finger sleeves ranging from 2.5 cm to 4 cm in length. Thereafter, some of the samples were trimmed around the edges of the sleeve and the inverted to place the seams on the inside. Moreover, other samples were provided a pull-on tab for aiding in placing the sleeve over a finger.

EXAMPLE 7

An appendage sleeve of the present invention was formed as described in Example 1. In this example, however, the finger sleeve was bidirectionally tapered with a length along the seams of 2.9 cm. The interior width of the sleeve at both ends was about 1.8 cm, while the width at the middle of the sleeve was about 2.1 cm to provide extra space for the knuckle of the finger.

EXAMPLE 8

The ability of an appendage sleeve of the present invention to be applied with a moisturizing agent for aiding in dry skin was demonstrated. An appendage sleeve similar to the one described in Example 7 was constructed. The resulting tapered finger sleeve had a length of 3.4 cm along the seams, an interior width at both ends of about 1.8 cm, and a width at the middle of the sleeve of about 2.0 cm. Thereafter, the sleeve was applied with a moisturizing lotion (KIMCARE7) and inverted to place the seams on the inside. The sleeve was then used to support a finger having dry skin.

EXAMPLE 9

The ability of an appendage sleeve of the present invention to cover an abrasion was demonstrated. An appendage sleeve as described in Example 7 was constructed. In this example, however, the coform base sheet was laminated to a quilted embossed structure base sheet prior to being welded to the stretch-bonded layer. The quilted embossed base sheet included an apertured film laminated to a surge layer. The apertured film was made from low density polyethylene and had a basis weight of 0.65 osy. The surge layer was a through air bonded bicomponent material and had a basis weight of 0.75 osy. The resulting laminate structure was then thermally bonded to a stretch-bonded laminate sheet to produce a tapered finger sleeve having a length of 3.0 cm. Thereafter, excess material was trimmed from the edges of the sleeve and the sleeve was inverted to place the seams on the inside. The interior width of one end of the sleeve was about 1.7 cm, while the width at the other end was about 1.8 cm. In addition, the width of the middle of the sleeve was about 2.0 cm to provide extra space for the knuckle or joint of a finger or toe. Furthermore, the sleeve was also provided with a pull-on tab for aiding in placing the sleeve over a finger. The formed finger sleeve was then used to cover an abrasion.

EXAMPLE 10

The ability of an appendage sleeve of the present invention to cover an abrasion was demonstrated. A spunbond/meltblown/spunbond (SMS) base sheet was laminated to the quilted embossed structure base sheet described in Example 9. The SMS base sheet had a total basis weight of 1.0 osy, wherein the meltblown interior layer had a basis weight of 0.4 osy. The SMS laminate was made from polypropylene fibers. The resulting laminate structure was then thermally bonded to the stretch-bonded laminate sheet described in Example 1 to produce a tapered finger sleeve having a length of 3.0 cm. Thereafter, excess material was trimmed from the edges of the sleeve and the sleeve was inverted to place the seams on the inside. The interior width of one end of the sleeve was about 1.8 cm, while the width at the other end was about 2.0 cm. Furthermore, the sleeve was also provided with a pull-on tab for aiding in placing the sleeve over a finger. The formed finger sleeve was then used to cover an abrasion by pressing the quilted embossed structure layer against the abrasion.

EXAMPLE 11

The ability of an appendage sleeve of the present invention to protect two swollen fingers was demonstrated. A neck-bonded laminate sheet was thermally bonded (in the shape of a finger) to a breathable film sheet to produce a conical finger sleeve that was open at both ends and was suitable for the insertion of two fingers. The neck-bonded laminate sheet was formed by adhesively bonding a metallocene-catalyzed polyethylene film between a pair of opposing polypropylene spunbond facings, providing a material with a total basis weight of 4.2 osy. The spunbond facings were extended to a width corresponding to 40% of their original width.

The breathable film sheet was made from a linear low density polyethylene containing a calcium carbonate filler. The film was stretched in order to create a microporous film. The film had a basis weight of 0.5 osy.

After being formed, the sleeve was inverted to place the seams on the inside. The length of the sleeve along the seams was 3.4 cm, while the interior width of the sleeve was about 3.2 cm (top) and about 3.5 cm (bottom). The formed two-fingered finger sleeve was then used to protect and partially immobilize (analogous to finger taping) a swollen finger.

EXAMPLE 12

The ability of an appendage sleeve of the present invention to cover a blister was demonstrated. A stretch bonded laminate as described in Example 1 was first folded upon itself, and then thermally bonded in a J-shape such that the top and one side were closed to form the wipe. The resulting sleeve had a tapered shape, with one surface longer than the other. The maximum width and length were approximately 2.4 cm and 5.7 cm, respectively. Excess material was then trimmed away from the edges of the wipe. The resulting sleeve was used to protect a blister.

EXAMPLE 13

The ability of an appendage sleeve of the present invention to protect an abrasion was demonstrated. An elastomeric, meltblown polyetherester (DEMIQUE7) base sheet was first chemically bonded (using hot melt adhesive, applied in the shape of a finger) to the coform base sheet described in Example 1. The polyetherester polymer was obtained from DSM Engineering Plastics. The meltblown polyetherester web had a basis weight of about 2 osy. Excess material was then trimmed away from the edges of the sleeve, which was then used to bandage an abrasion on a finger.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A device for treating appendage ailments comprising:
a base web comprising a nonelastic nonwoven web of fibrous material, the base web being laminated with an elastic layer, said base web and said elastic layer defining a sleeve, the sleeve having a shape configured to conform to the shape of a finger or toe of a user, said sleeve having a distal end and a proximal end with one of said distal or said proximal ends being open and configured to allow the insertion of an appendage into said sleeve through said open end, the sleeve defining an interior surface and an exterior surface, the interior surface configured to be placed adjacent an appendage when inserted into the sleeve, the elastic layer for providing the sleeve with form-fitting properties and wherein the nonelastic nonwoven web forms the interior surface of the sleeve, said sleeve comprising a first panel attached to a second panel, the panels forming seams that extend alone the length of the sleeve.

2. A device as defined in claim 1, wherein said sleeve is tapered to better fit onto said finger or toe.

3. A device as defined in claim 1, wherein said distal end and said proximal end are open such that said open proximal end is adapted to allow the insertion of said finger or toe, said open distal end being adapted to receive said finger or toe inserted at said open proximal end such that said finger or toe can be inserted through said sleeve.

4. A device as defined in claim 1, wherein said nonwoven web is selected from the group consisting of spunbonded fiber webs, meltblown fiber webs, spunbonded/meltblown/spunbonded fiber webs, spunbonded/meltblown fiber webs, and bonded carded webs.

5. A device as defined in claim 1, wherein the elastic layer comprises an elastomeric material.

6. A device as defined in claim 5, wherein said nonwoven web comprises a thermoplastic polymer.

7. A device as defined in claim 6, wherein said nonwoven web further comprises pulp fibers.

8. A device as defined in claim 5, wherein said elastic layer comprises a fibrous material.

9. A device as defined in claim 5, wherein said elastic layer comprises a film.

10. A device as defined in claim 5, wherein said elastic layer comprises a foam.

11. A device as defined in claim 5, wherein said sleeve comprises a stretch-bonded laminate.

12. A device as defined in claim 5, wherein said sleeve comprises a neck-bonded laminate.

13. A device as defined in claim 1, further comprising a moisture barrier being incorporated onto at least a portion of said base web, said moisture barrier being substantially impermeable to liquids when contacted therewith.

14. A device as defined in claim 13, wherein said moisture barrier is vapor-permeable.

15. A device as defined in claim 13, wherein said moisture barrier comprises a plastic film.

16. A device as defined in claim 13, wherein said plastic film is a microporous film.

17. A device as defined in claim 13, wherein said moisture barrier comprises a multi-layered laminate.

18. A device as defined in claim 17, wherein one of said layers of said moisture barrier comprises a nonwoven web of fibrous material.

19. A device as defined in claim 17, wherein one of said layers of said moisture barrier comprises a vapor-permeable film.

20. A device as defined in claim 1, said base web being applied with an additive selected from the group consisting of an antibiotic, an anti-microbial agent, an anti-inflammatory agent, a moisturizing agent, a topical analgesic, a vasodilator, a corticosteroid, dimethyl sulfoxide, capsaicin, menthol, methyl salicylate, neosporin, a cationic polymer, an anti-fungal agent, and combinations thereof.

21. A device as defined in claim 20, wherein said base web is treated with a cationic polymer, said cationic polymer comprising chitosan.

22. A device as defined in claim 20, wherein said base web is treated with an anti-inflammatory agent, said anti-inflammatory agent comprising a cyclooxygenase-1 inhibitor.

23. A device as defined in claim 20, wherein said base web is treated with an anti-inflammatory agent, said anti-inflammatory agent comprising a cyclooxygenase-2 inhibitor.

24. A device for treating appendage ailments comprising:
a hollow sleeve member having an open end for the insertion of a finger or toe and having a shape configured to conform to the shape of a finger or toe of a user, said sleeve member comprising an elastic nonwoven material, said elastic nonwoven material being capable of being stretched and contracted for providing said sleeve member with form fitting properties, the elastic nonwoven material being laminated with a nonelastic nonwoven web, the sleeve member defining an interior surface and an exterior surface, the interior surface configured to be placed adjacent an appendage when inserted into the sleeve member, the nonelastic nonwoven web forming the interior surface, said sleeve member comprising a first panel attached to a second panel, the panels forming seams that extend along the length of the sleeve.

25. A device as defined in claim 24, wherein said sleeve member is tapered to better fit onto said finger or toe.

26. A device as defined in claim 24, wherein said nonelastic nonwoven web is selected from the group consisting of spunbonded fiber webs, meltblown fiber webs, spunbonded/meltblown/spunbonded fiber webs, spunbonded/meltblown fiber webs, and bonded carded webs.

27. A device as defined in claim 24, wherein said sleeve member comprises a stretch-bonded laminate.

28. A device as defined in claim 24, wherein said sleeve member comprises a neck-bonded laminate.

29. A device as defined in claim 24, further comprising a moisture barrier being incorporated into at least a portion of said sleeve member, said moisture barrier being substantially impermeable to liquids when contacted therewith.

30. A device as defined in claim 24, said sleeve member being applied with an additive selected from the group consisting of an antibiotic, an anti-microbial agent, an anti-inflammatory agent, a moisturizing agent, a topical analgesic, a vasodilator, a corticosteroid, dimethyl sulfoxide, capsaicin, menthol, methyl salicylate, neosporin, a cationic polymer, an anti-fungal agent, and combinations thereof.

31. A device for treating appendage ailments comprising:
a hollow sleeve member having a first open distal end and a second open proximal end spaced from said distal end, said sleeve member having a shape configured to receive a finger or a toe, said sleeve member comprising a first panel attached to a second panel, the panels forming seams that extend along the length of the sleeve, the first panel comprising an elastic nonwoven material, said elastic nonwoven material capable of being stretched and contracted for providing said sleeve member with form fitting properties, the second panel comprising a nonwoven web, the nonwoven web defining at least a portion of an interior surface of the hollow sleeve.

32. A device as defined in claim 31, wherein the nonwoven web of said second panel is non-elastic.

33. A device as defined in claim 31, wherein said sleeve member is tapered.

34. A device as defined in claim 31, wherein said elastic nonwoven material comprises a material selected from the group consisting of stretch bonded laminates and neck bonded laminates.

35. A device as defined in claim 31, wherein said sleeve member is applied with an additive selected from the group consisting of an antibiotic, an anti-microbial agent, an anti-inflammatory agent, a topical analgesic, a vasodilator, a moisturizing agent, a corticosteroid, dimethyl sulfoxide capsaicin, neosporin, a cationic polymer, an anti-fungal agent, and combinations thereof.

* * * * *

UNITED STATES PATENT AND TRADEMARK OFFICE
CERTIFICATE OF CORRECTION

PATENT NO. : 7,012,169 B2
APPLICATION NO. : 09/826371
DATED : March 14, 2006
INVENTOR(S) : Jason P. McDevitt et al.

It is certified that error appears in the above-identified patent and that said Letters Patent is hereby corrected as shown below:

Column 25, line 50 (Claim 1) "that extend alone the length" should read --that extend along the length--

Signed and Sealed this

Twenty-ninth Day of August, 2006

JON W. DUDAS
*Director of the United States Patent and Trademark Office*